US009334212B2

(12) United States Patent
Subramanyam et al.

(10) Patent No.: US 9,334,212 B2
(45) Date of Patent: May 10, 2016

(54) COMPOUNDS AND COMPOSITIONS

(75) Inventors: Ravi Subramanyam, Mumbai (IN); Guofeng Xu, Plainsboro, NJ (US); Jennifer Gronlund, Flemington, NJ (US); Shamim Ansari, Princeton, NJ (US)

(73) Assignee: Colgate-Palmolive Company, New York, NY (US)

(*) Notice: Subject to any disclaimer, the term of this patent is extended or adjusted under 35 U.S.C. 154(b) by 394 days.

(21) Appl. No.: 13/996,038

(22) PCT Filed: Dec. 21, 2010

(86) PCT No.: PCT/US2010/061428
§ 371 (c)(1),
(2), (4) Date: Jun. 20, 2013

(87) PCT Pub. No.: WO2012/087289
PCT Pub. Date: Jun. 28, 2012

(65) Prior Publication Data
US 2013/0280185 A1 Oct. 24, 2013

(51) Int. Cl.
*C07C 39/373* (2006.01)
*A61K 8/34* (2006.01)
*A61Q 11/00* (2006.01)
*A61Q 19/06* (2006.01)

(52) U.S. Cl.
CPC .............. *C07C 39/373* (2013.01); *A61K 8/347* (2013.01); *A61Q 11/00* (2013.01); *A61Q 19/06* (2013.01)

(58) Field of Classification Search
CPC .................................................. C07C 37/737
See application file for complete search history.

(56) References Cited

U.S. PATENT DOCUMENTS

| 3,720,721 | A | 3/1973 | Becker et al. |
| 3,956,403 | A | 5/1976 | Orlando et al. |
| 5,776,435 | A | 7/1998 | Gaffar et al. |
| 7,435,837 | B2 | 10/2008 | Gross et al. |
| 2006/0241172 | A1 | 10/2006 | Zhou et al. |
| 2007/0041914 | A1 | 2/2007 | Gaffar et al. |
| 2007/0048235 | A1 | 3/2007 | Harmalker et al. |

FOREIGN PATENT DOCUMENTS

| EP | 0382213 | 5/1995 |
| JP | 9-278638 | 10/1997 |
| WO | WO 97/20878 | 6/1997 |
| WO | WO 01/85116 | 11/2001 |
| WO | WO 2006/066060 | 6/2006 |
| WO | WO 2006/101818 | 9/2006 |
| WO | WO 2006/116165 | 11/2006 |
| WO | WO 2009/066060 | 5/2009 |
| WO | WO 2011/106003 | 9/2011 |
| WO | WO 2011/106492 | 9/2011 |
| WO | WO 2011/106493 | 9/2011 |
| WO | WO 2012/015408 | 2/2012 |

OTHER PUBLICATIONS

Fujita et al., 1972, "Honokiol, A New Phenolic Compound Isolated from the Bark of Magnolia Obovata," CA Plus Database AN: 1972:112819, Chem. And Pharmaceutical Bulletin 20(1):212-213.
Huddle et al., 1981, "Reactions of Alklyllithium Compounds with Aryl Halides," CA Plus Databse AN: 1981:12100 12:2617-2625.
International Search Report and Written Opinion in International Application No. PCT/US2010/061428, mailed Sep. 20, 2011.
Kirste et al., 2009, "Ortho-Selective Phenol-Coupling Reaction by Anodic Treatment on Boron-Doped Diamond Electrode Using Fluorinated Alcohols," CA Plus Database AN: 2009:314228, European J. 15(10):2273-2277.
Kraft, 1950, "Constitutional Connections in the Field of Bacteriostatically Active Compounds," CA Plus Database AN: 1950:56808, Pharmacie 5:257-259.
Kushioka, 1984, "Autoxidation of Phenols Catalyzed by Copper(II)-Ethylenediamine Complexes: The Reaction Mechanism," CA Plus Database AN: 1984:610290, J. Organic Chemistry 49(23):4456-4459.
Marsh et al., 1949, "Fungicidal Activity of Bisphenols," Industrial and Engineering Chemistry, 41(10):2176-2184.
Sugii, 1930, "Constituents of the Bark of Magnolia officinalis, Rhed. Et Wils and Magnolia obovata, Thumb," 1930, CA Plus Database AN: 1930:32868 Yakugaku Zasshi 50:183-217.
Written Opinion in International Application No. PCT/US2010/061428, mailed Nov. 28, 2012.

*Primary Examiner* — Benjamin Packard

(57) ABSTRACT

Described herein are compounds of Formula (I): or a salt thereof; wherein: R1 and R5 are independently selected from H, OH and alkoxy; $R_2$-$R_4$ and $R_6$-$R_8$ are independently selected from H, OH, F, Cl, Br, and I; $R_9$ and $R_{10}$ are independently selected from H, alkyl, alkenyl, alkynyl, and aryl; with the proviso that: at least one of $R_1$ and $R_5$ is OH or alkoxy; and at least one of $R_2$-$R_4$ and $R_6$-$R_8$ is F, Cl, Br or I; compositions comprising said compounds; and methods of making and using the same.

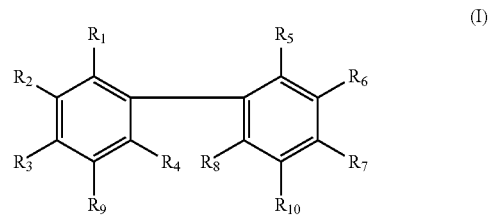

18 Claims, No Drawings

COMPOUNDS AND COMPOSITIONS

BACKGROUND

There is an ongoing need for antibacterial agents and compositions comprising the same, which have efficacy against common oral pathogens and skin bacteria.

SUMMARY

In some embodiments, the present invention provides a compound of Formula (I):

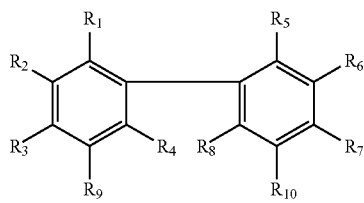

or a salt thereof; wherein: $R_1$ and $R_5$ are independently selected from H, OH and alkoxy; $R_2$-$R_4$ and $R_6$-$R_8$ are independently selected from H, OH, F, Cl, Br, and I; $R_9$ and $R_{10}$ are independently selected from H, alkyl, alkenyl, alkynyl, and aryl; provided that: at least one of $R_1$, $R_5$ or $R_7$ is OH or alkoxy; and at least one of $R_2$-$R_4$, $R_6$ and $R_9$ is F, Cl, Br or I; and a carrier.

In some embodiments, the compound of Formula (I) has the structure of Formula (II):

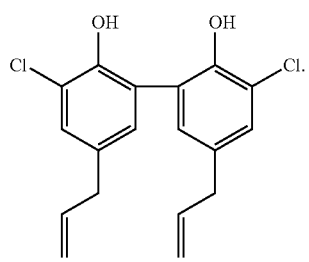

Some embodiments provide a method of treating or preventing a disease or condition of the oral cavity comprising contacting an oral cavity surface with any one of the compositions described herein. Other embodiments provide a method of treating or preventing a disease or condition of the skin comprising contacting a skin surface of a subject in need thereof with any one of the compositions described herein.

DETAILED DESCRIPTION

As used throughout, ranges are used as shorthand for describing each and every value that is within the range. Any value within the range can be selected as the terminus of the range.

All references cited herein are hereby incorporated by reference in their entireties.

In the event of a conflict in a definition in the present disclosure and that of a cited reference, the present disclosure controls.

As used herein, the term "alkyl" refers to a saturated aliphatic hydrocarbon, including straight-chain, branched-chain, and cycloalkyl groups of 1 to 20 carbon atoms, e.g. propyl, isopropyl, butyl, cyclopropyl.

As used herein, the term "alkenyl" refers to an unsaturated, open chain hydrocarbon with one or more carbon-carbon double bonds, having the general formula $C_nH_{2n}$, e.g. vinyl and propenyl.

As used herein, the term "alkynyl" refers to an unsaturated aliphatic hydrocarbon containing at least one triple bond in the carbon chain, e.g. acetylene.

As used herein, the term "cycloalkyl" refers to a $C_{3-8}$ cyclic hydrocarbon, e.g. cycloalkyl or cyclopropyl.

As used herein, the term "alkoxy" refers to an alkyl group of indicated number of carbon atoms attached to the parent molecular moiety through an oxygen bridge, e.g. methoxy or ethoxy.

Some embodiments provide a compound of Formula (I):

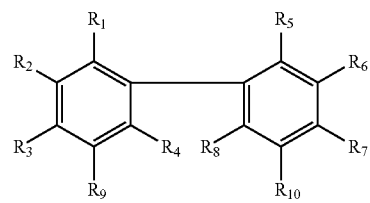

or a salt thereof; wherein: $R_1$ and $R_5$ are independently selected from H, OH and alkoxy; $R_2$-$R_4$ and $R_6$-$R_8$ are independently selected from H, OH, F, Cl, Br, and I; $R_9$ and $R_{10}$ are independently selected from H, alkyl, alkenyl, alkynyl and aryl; with the proviso that: at least one of $R_1$, $R_5$ and $R_7$ is OH or alkoxy; and at least one of $R_2$-$R_4$, $R_6$ and $R_5$ is F, Cl, Br or I.

Some embodiments provide a compound wherein $R_1$ and $R_5$ are independently selected from OH or alkoxy; and $R_2$ and $R_6$ are independently selected from H, F, Cl, Br and I. Other embodiments provide a compound wherein $R_1$ and $R_5$ are OH. Further embodiments provide a compound wherein $R_1$ and $R_7$ are OH. Yet other embodiments provide a compound wherein $R_2$ and $R_6$ are Cl.

Some embodiments provide a compound wherein $R_9$ and $R_{10}$ are independently selected from $C_2$-$C_8$ alkyl and $C_2$-$C_8$ alkenyl. Some embodiments provide a compound having the structure of Formula (II):

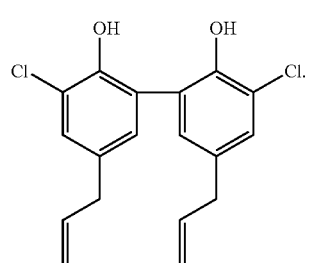

Some embodiments provide a compound having the structure of Formula (III):

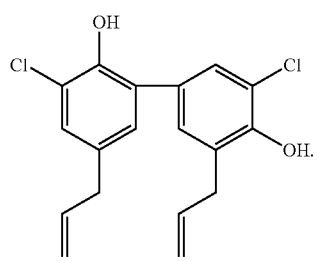

Some embodiments of the present invention provide an oral or personal care composition comprising: a compound of Formula (I):

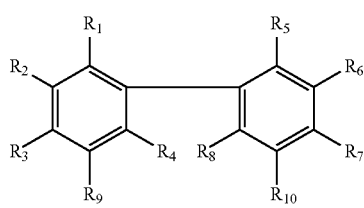

or a salt thereof; wherein: $R_1$ and $R_5$ are independently selected from H, OH and alkoxy; $R_2$-$R_4$ and $R_6$-$R_8$ are independently selected from H, OH, F, Cl, Br, and I; $R_9$ and $R_{10}$ are independently selected from H, alkyl, alkenyl, alkynyl, and aryl; with the proviso that: at least one of $R_1$, $R_5$ and $R_7$ is OH or alkoxy; and at least one of $R_2$-$R_4$, $R_6$ and $R_8$ is F, Cl, Br or I; and a carrier. In some embodiments, the carrier is an orally acceptable carrier. In some embodiments, the carrier is a carrier suitable for a personal care composition.

Components/ingredients suitable for preparing a personal care carrier are described, for example, in U.S. Patent Application Publication No. US 2007/0048235. Some embodiments provide a composition comprising any one of the compounds described herein.

In some embodiments, $R_1$ and $R_5$ are independently selected from OH or alkoxy; and $R_2$ and $R_6$ are independently selected from H, F, Cl, Br and I. In some embodiments, $R_1$ and $R_5$ are OH. In other embodiments, $R_1$ and $R_7$ are OH. Still other embodiments provide compositions wherein $R_2$ and $R_6$ are Cl.

In further embodiments, $R_9$ and $R_{10}$ are independently $C_2$-$C_8$ alkyl or $C_2$-$C_8$ alkenyl. Yet other embodiments provide compositions wherein the compound of Formula (I) has the structure of Formula (II):

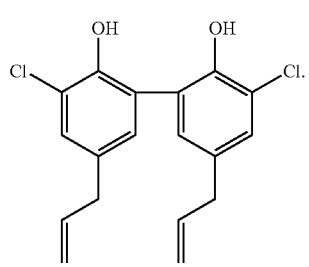

While other embodiments provide compositions wherein the compound of Formula (I) has the structure of Formula (III):

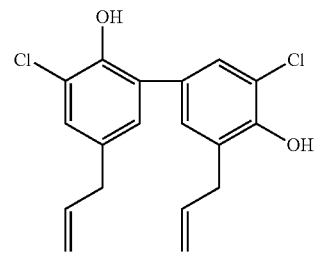

In some embodiments, the present invention provides compositions wherein the compound of Formula (I) is present at a concentration of from about 0.001 to about 10%, by weight. Other embodiments provide compositions wherein the compound of Formula (I) is present at a concentration of from about 0.01 to about 5%, by weight. While other embodiments provide compositions wherein the compound of Formula (I) is present at a concentration of from about 0.1 to about 2%, by weight. Still other embodiments provide compositions wherein the compound of Formula (I) is present at a concentration of about 0.5%, by weight.

In some embodiments, the composition further comprises one or more components selected from a fluoride ion source; a tartar control agent; a buffering agent; an abrasive; and a combination of two or more thereof. In some embodiments, at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.

Some embodiments provide a method of treating or preventing a disease or condition of the oral cavity comprising contacting an oral cavity surface with any one of the compositions described herein. In some embodiments, the disease or condition of the oral cavity includes a disease or condition of the teeth, oral mucosa, gingiva or tongue. In some embodiments, the disease or condition of the oral cavity is selected from caries, gingivitis, periodontitis and halitosis.

In some embodiments, the present invention provides a method of treating or preventing a disease or condition of the skin comprising contacting the skin surface of a subject in need thereof with any one of the compositions described herein. In some embodiments, the disease or condition is selected from: body odor, erythrasma, acne, impetigo, boils, folliculitis, cellulitis, carbuncles, and scalded skin syndrome.

In some embodiments, the method comprises repeating the application of the composition multiple times until the desired anti-bacterial effects are achieved in the subject. In some embodiments, the composition is applied daily for a period of several days, e.g. at least one week.

In some embodiments, the compound of Formula (I) is a compound selected from:

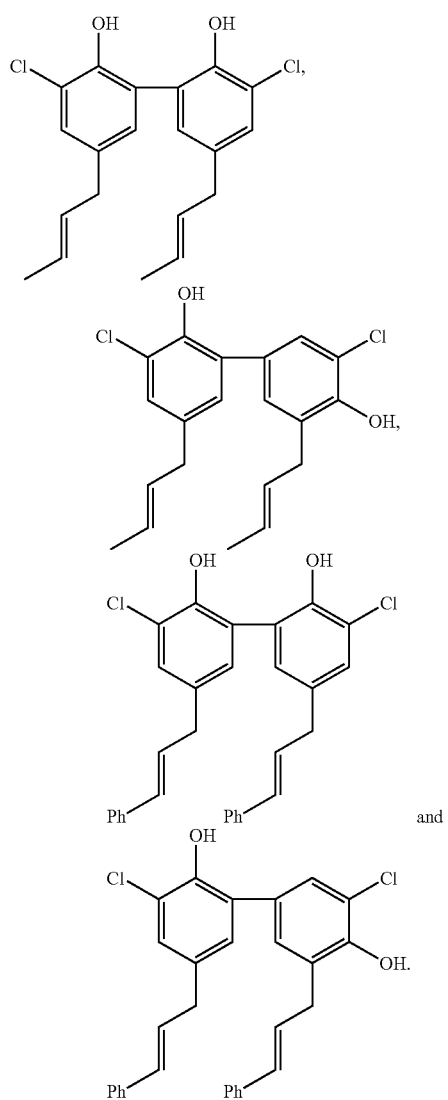

In some embodiments, the composition further comprises an active compound from an extract of magnolia selected from: magnolol, honokiol, tetrahydromagnolol, tetrahydrohonokiol, and a combination of two or more thereof.

Suitable carriers include the conventional and known carriers used in making toothpastes, tooth powders, prophylaxis pastes, mouth rinses, lozenges, gums, beads, and the like. As those skilled in the art will appreciate, the selection of specific carrier components is dependent on the desired product form, including toothpastes, tooth powders, prophylaxis pastes, mouth rinses, lozenges, gums, gels, paints, confectionaries, and the like.

In some embodiments, the oral composition further comprises one or more components selected from cleaning agents, flavoring agents, sweetening agents, anti-adhesion agents, surfactants, foam modulators, abrasives, pH modifying agents, humectants, moisturizers, mouth feel agents, colorants, abrasives, preservatives, a fluoride ion source, a saliva stimulating agent, emollients, viscosity modifiers, diluents, emulsifiers, nutrients and combinations thereof. Other optional additives may be included.

Colorants such as dyes may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl)indanedione, FD&C Yellow No. (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[N-ethyl-N-p-sulfobenzyl)-DELTA-3,5-cyclohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants if included are present in very small quantities.

Suitable flavoring agents include, but are not limited to, natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavoring agents can be used individually or in admixture. Commonly used flavors include mints such as peppermint, artificial vanilla, cinnamon derivatives, and various fruit flavors, whether employed individually or in admixture. Generally, any flavoring agent or food additive, such as those described in Chemicals Used in Food Processing, publication 1274 by the National Academy of Sciences, pages 63-258, may be used. Typically, flavoring agents, if included, are present at a concentration of from about 0.01 to about 1%, by weight. In some embodiments, the flavoring agent may be present at a concentration of about 0.2%, by weight.

Sweeteners include both natural and artificial sweeteners. Suitable sweeteners include water soluble sweetening agents such as monosaccharides, disaccharides and polysaccharides such as xylose, ribose, glucose (dextrose), mannose, galactose, fructose (levulose), sucrose (sugar), maltose, water soluble artificial sweeteners such as the soluble saccharin salts, i.e., sodium or calcium saccharin salts, cyclamate salts dipeptide based sweeteners, such a L-aspartic acid derived sweeteners, such as L-aspartyl-L-phenylalanine methyl ester (aspartame). In general, the effective amount of sweetener is utilized to provide the level of sweetness desired for a particular composition, will vary with the sweetener selected. This amount will normally be from about 0.001 to about 5%, by weight. In some embodiments, the sweetener is sodium saccharin and is present at a concentration of about 0.01%, by weight.

Whitening agents, material which is effective to effect whitening of a tooth surface to which it is applied, such as hydrogen peroxide and urea peroxide, high cleaning silica, preservatives, silicones, and chlorophyll compounds may be incorporated into the compositions of the present invention. In various embodiments, the compositions of this invention comprise a peroxide whitening agent, comprising a peroxide compound. A peroxide compound is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In some embodiments, the peroxide compound comprises hydrogen peroxide. In some embodiments, the peroxide compound consists essentially of hydrogen peroxide. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite. One or more whitening agents are optionally present in a tooth-whitening effective total amount. In some embodiments the whitening agent is separated from the aqueous carrier. In some embodiments the whitening agent is separated from the aqueous carrier by encapsulation of the whitening agent.

Optionally, breath freshening agents may be provided. Any orally acceptable breath freshening agent can be used, including without limitation zinc salts such as zinc gluconate, zinc citrate, zinc oxide and zinc chlorite, alpha-ionone and mixtures thereof. One or more breath freshening agents are optionally present in a breath freshening effective total amount.

Optionally, the composition may include a tartar control (anticalculus) agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J. In some embodiments, a phosphate is present at a concentration of from about 0.01 to about 10%, by weight. In some embodiments, a phosphate is present at a concentration of from about 1%, by weight.

Some embodiments provide compositions wherein a buffering agent is present. In some embodiments, sodium phosphate monobasic is present at a concentration of from about 0.01 to about 5%, by weight. In some embodiments, sodium phosphate monobasic phosphate is present at a concentration of about 1%, by weight. In some embodiments, sodium phosphate dibasic is present at a concentration of from about 0.01 to about 5%, by weight. In some embodiments, sodium phosphate dibasic phosphate is present at a concentration of about 0.15%, by weight.

Other optional additives include antimicrobial (e.g., antibacterial) agents. Any orally acceptable antimicrobial agent can be used, including Triclosan (5-chloro-2-(2,4-dichlorophenoxy)phenol); 8-hydroxyquinoline and salts thereof, zinc and stannous ion sources such as zinc citrate, zinc sulfate and zinc gluconate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride,); bisguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; grapeseed extract; thymol; eugenol; menthol; geraniol; carvacrol; citral; eucalyptol; catechol; 4-allylcatechol; hexyl resorcinol; methyl salicylate. A further illustrative list of useful antibacterial agents is provided in U.S. Pat. No. 5,776,435, Gaffar, et al., issued Jul. 7, 1998. In some embodiments, the antimicrobial agent is present at a concentration of from about 0.001 to about 1%, by weight. In some embodiments, the antimicrobial agent is cetylpyridinium chloride. In some embodiments, cetylpyridinium chloride is present at a concentration of from about 0.001 to about 1%, by weight. In other embodiments, cetylpyridinium chloride is present at a concentration of about 0.05%, by weight.

Abrasives are another class of optional additives. Suitable abrasives include without limitation, silica, for example in the form of silica gel, hydrated silica or precipitated silica, alumina, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate.

Antioxidants are another class of optional additives. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Also optional, a saliva stimulating agent, useful for example in amelioration of dry mouth, may be included. Any orally acceptable saliva stimulating agent can be used, including without limitation food acids such as citric, lactic, malic, succinic, ascorbic, adipic, fumaric, and tartaric acids, and mixtures thereof. One or more saliva stimulating agents are optionally present in a saliva stimulating effective total amount.

Optionally, an antiplaque (e.g., plaque disrupting) agent may be included. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

Optional desensitizing agents include potassium citrate, potassium chloride, potassium tartrate, potassium bicarbonate, potassium oxalate, potassium nitrate, strontium salts, and mixtures thereof.

Optional additives also include vitamins, herbs and proteins. Vitamins include Vitamins C and D, thiamine, riboflavin, calcium pantothenate, niacin, folic acid, nicotinamide, pyridoxine, cyanocobalamin, para-aminobenzoic acid, bioflavonoids, pantheon, retinyl palmitate, tocopherol acetate, and mixtures thereof. Herbs such as *Chamomilla recutita*, *Mentha piperita*, *Salvia officinalis*, and *Commiphora myrrha* may optionally be included. Suitable proteins include milk proteins and enzymes such as peroxide-producing enzymes, amylase, plaque-disrupting agents such as papain, glucoamylase, glucose oxidase, and "next generation" enzymes."

*S. aureus* can cause a range of illnesses from minor skin infections, such as pimples, impetigo, boils, cellulites, carbuncles, scalded skin syndrome, and abscesses, to life threatening diseases such as pneumonia, meningitis, osteomylitis, endocarditis, toxic shock syndrome, and sepsis. *S. aureus* is also often responsible for nosocomial infections.

*C. minutissimum* and *C. xerosis* are known to be involved in the generation of body odor. *C. minutissimum* is also associated with erythrasmas.

Embodiments of the present invention are further described in the following examples. The examples are merely illustrative and do not in any way limit the scope of the invention as described and claimed.

EXAMPLES

Example 1

Compounds of the present invention can be prepared by chlorinating a biphenyl precursor, such as magnolol or honokiol, with a chlorinating agent in a solvent.

For example, a biphenyl precursor can be reacted with chlorine in an inert solvent at a temperature of from about 0 to about 100° C., preferably from about 10 to about 80° C., and more preferably from about 10 to about 50° C. The chlorination is achieved optionally in the presence of a catalyst.

The biphenyl precursor can be reacted with dichloroethane or acetic acid at room temperature for about 2 to about 10 hours to obtain a mixture of a chlorinated biphenyl compounds. The mixture is subjected to chromatography and each product is isolated according to methods known to those skilled in the art.

Example 2

Table 1 (below) describes the antibacterial efficacy of an exemplary compound of the present invention against common oral pathogens, *A. viscosus* and *S. mutans*.

TABLE 1

| | Minimum Inhibitory Concentration (ppm) | | |
|---|---|---|---|
| Bacterium | Compound of Formula (II) | Magnolol | Triclosan |
| *A. viscosus* | 0.5-1.0 | 32 | 1-2 |
| *S. mutans* | 0.5-1.0 | 32 | 1-2 |

Example 3

The compound of Formula (II) was evaluated for its antibacterial efficacy against representative skin bacteria such as *Staphylococcus aureus* (*S. aureus*), *Staphylococcus epidermidis* (*S. epidermidis*), *Corynebacterium minutissimum* (*C. minutissimum*), *Corynebacterium xerosis* (*C. xerosis*) and *Escherichia coli* (*E. coli*). Zone of inhibition (ZOI), Minimum Inhibitory Concentration (MIC), and a Short Interval Kill Test (SIKT) were all performed, and the results are described in Tables 2-4 (below).

A. Zone of Inhibition Test (ZOI)

The compound of Formula (II) was dissolved in polyethylene glycol (PEG 300), or in 100% ethanol at 0.5% concentration. 20 μL of each solution was placed on separate filter disks and air dried for 20 minutes. After 20 minutes of drying, the coated disks were placed in the bacterial lawn and plates were incubated at 37° C. for 18 hours, followed by measurement of ZOI. The results are provided in Table 2 (below).

TABLE 2

| | Zone of Inhibition (mm) | | | |
|---|---|---|---|---|
| Active | *S. aureus* | *S. epiderm.* | *C. minutissimum* | *C. xerosis* |
| 0.5% Compound of Formula (II) + PEG 300 | 15 | 16 | 21 | 15 |
| 0.5% Compound of Formula (II) + EtOH | 13 | 15 | 17 | 14 |
| PEG 300 | 0 | 0 | 0 | 0 |
| EtOH | 0 | 0 | 0 | 0 |

The data described in Table 2 demonstrates the antibacterial efficacy of the compound of Formula (II) against four common skin bacteria—*S. aureus* and *S. epidermidis* (skin and soft tissue infections); and *C. minutissimum* and *C. xerosis* as (odor-causing bacteria).

B. Minimum Inhibitory Concentration (MIC)

MIC against four common skin pathogens was evaluated for the compound of Formula (II), using the following method: A two-fold dilution of the compound of Formula (II) was prepared in a 96 well plate and a constant amount of bacteria added in each well. After 18-24 hours of incubation, bacterial growth was measured by using a Spectrophotometric Micro-plate Reader and the MIC values were determined. Results are provided in Table 3 (below).

TABLE 3

| | Minimum Inhibitory Concentration (ppm) | | | |
|---|---|---|---|---|
| Active | *S. aureus* | *S. epiderm.* | *C. minutissimum* | *C. xerosis* |
| Compound of Formula (II) + PEG 300 | 19.5 | 39 | 9.77 | 78 |
| Compound of Formula (II) + EtOH | 39 | 39 | 39 | 156 |
| PEG 300 | 156 | 156 | 156 | 625 |
| EtOH | 312 | 625 | 625 | 1250 |
| Triclosan | <2.44 | <2.44 | 4.88 | 9.76 |

The results described in Table 3 (above) further demonstrate the anti-bacterial efficacy of the compound of Formula (II) against common skin pathogens.

C. Short Interval Kill Test (SIKT)

SIKT determines the kill effect of the test article at a predetermined exposure time. This test determines the kill effect of the test article at a predetermined exposure time. Briefly, 1.2 mL of the compound of Formula (II)+PEG 300 was transferred into a sterile test tube, to which 0.2 mL of a freshly prepared bacterial suspension (OD adjusted to 0.1 at 620 nm) was added and gently mixed. The reaction was neutralized at the 1 minute or at the 5 minute point by adding a neutralizing broth. The reaction mixture was further diluted with letheen broth in 10-fold fashion and plated on MCA (Microbial Count Agar) plates for viable bacterial count. The results are provided in Table 4 (below).

TABLE 4

| | Time | |
|---|---|---|
| Active | 1 minute | 5 minute |
| 0.5% Compound of Formula (II) + PEG 300 | 65.18 | 87.37 |
| 0.5% TCC | 56.54 | 74.11 |

The data described in Table 4 (above) is further evidence of the antibacterial efficacy of the compound of Formula (II).

Example 4

The antibacterial efficacy of the compound of Formula (II) was measured in comparison to triclosan, using various tests. The results are provided below in Tables 5 and 6.

TABLE 5

| | Zone of Inhibition (mm) | | |
|---|---|---|---|
| Active | S. aureus | C. minutissimum | E. coli |
| 0.5% Compound of Formula (II) | 20 | 22 | 0 |
| 0.15% Triclosan | 50 | 21 | 40 |

TABLE 6

| | Minimum Inhibitory Concentration (ppm) | | |
|---|---|---|---|
| Active | S. aureus | C. minutissimum | E. coli |
| 0.5% Compound of Formula (II) | 2.44 | 9.7 | 1250 |
| 0.15% Triclosan | <2.44 | 4.88 | <2.44 |

Example 5

Rapid Agar Plate Assay (RAPA)

The compound of Formula (II) was mixed with a base bar soap chip and tested for any residual antibacterial activity against S. aureus and E. coli by a rapid agar plate assay (RAPA). Briefly, the method involves washing TSA plates with the soap samples for 10 seconds, lathering for another 40 seconds and finally rinsing for 10 seconds. After air drying for 30 minutes, 100 µL of freshly prepared bacterial suspension (density was adjusted to 0.1 OD at 620 nm) was applied on the treated plates and then plates were incubated at 37° C. for about 18 hours. TSA plates washed with normal tap water were used as negative control. Next day, bacterial colonies were counted and converted to log 10 and the log reductions as a result of washing with samples were calculated. The results are summarized in Table 7 (below).

TABLE 7

| | Log reduction in Bacterial Count | |
|---|---|---|
| Active | E. Coli | S. aureus |
| 0.5% Compound of Formula (II) in soap chip | 0.09 | 0.506 |
| Soap Chip | 0.004 | 0.021 |
| 0.25% Triclosan bar | 2.387 | 2.409 |
| 0.4% TCC bar | 0.167 | 2.409 |

The data described in Table 7 (above) demonstrates that a bar soap chip containing 0.5% of a compound of Formula (II) inhibited the growth of S. aureus by 0.5 log which is >50% reduction in the growth of this particular organism.

Example 6

Table 8 (below) provides the formulation of an exemplary oral care composition of the present invention.

TABLE 8

| Ingredient | % w/w |
|---|---|
| Water | 30 |
| Sorbitol | 30 |
| Glycerin | 15 |
| Zeodent 114 | 11 |
| Zeodent 105 | 10 |
| Sodium carboxymethylcellulose | 1.1 |
| Flavor | 1 |
| Titanium dioxide | 0.5 |
| Compound of Formula (II) | 0.5 |
| Carrageenan | 0.4 |
| Sodium saccharin | 0.3 |
| Sodium fluoride | 0.24 |

The formulation described in Table 8 (above) can be prepared by methods known in the art. An exemplary method is provided below.

Two premixes can be made. Sodium saccharin, sodium sulfate and fluoride are dissolved in water to form premix 1. The compound of Formula (II) is added to the flavor component and mixed until dissolved or dispersed, to form premix 2. Gums (carboxymethyl cellulose and carrageenan) and titanium dioxide are dispersed in glycerin and mixed for 5 minutes. Sorbitol is added and the combination is mixed for an additional 5 minutes. The resultant mixture comprises a gel phase. Premix 1 is then added to the gel phase, and mixed for about 5 minutes. The gel phase is transferred to a Ross mixer, where the silicas are added and mixed for about 20 minutes at high speed with vacuum. Premix 2 and sodium lauryl sulfate is then added to the Ross mixer, wherein the combination is wet mixed for about 10 minutes at low speed with vacuum.

Example 7

The compositions described in Tables 9 and 10 (below) can be prepared according to known methods for preparing personal care compositions, for example, those described in U.S. Patent Application Publication No. 2007/0048235. Table 9 provides the formulation of an exemplary liquid soap composition of the present invention.

TABLE 9

| Ingredient | % w/w |
| --- | --- |
| Water | 68.3 |
| Sodium alpha olefin sulfonate | 22.3 |
| Lauramide DEA | 3.1 |
| Cocoamidopropyl betaine | 3.1 |
| Sodium chloride | 0.6 |
| Polyquaternium-7 | 1 |
| DMDM Hydatoin | 0.4 |
| Fragrance | 0.3 |
| Citric acid | 0.3 |
| Compound of Formula II | 0.5 |
| Tetrasodium EDTA | 0.1 |
| Aloe vera gel | 0.01 |
| Glycerin | 0.01 |

Table 10 (below) describes the formulation of an exemplary bar soap composition of the present invention.

TABLE 10

| Ingredient | % w/w |
| --- | --- |
| Tallow/Lauric acid soap chips | 96.7 |
| Fragrance | 1.25 |
| Diethylenetriaminepentaacetic acid, pentasodium salt | 0.025 |
| Etidronic acid | 0.017 |
| Citric acid | 0.5 |
| Compound of Formula II | 0.5 |
| Extrapone seaweed | 0.05 |
| Tinopal CBS-X | 0.005 |
| Titanium dioxide | 0.8 |
| Softben-10 Green ASF 14 | 0.2 |

As those skilled in the art will appreciate, numerous changes and modifications may be made to the embodiments described herein without departing from the spirit of the invention. It is intended that all such variations fall within the scope of the appended claims.

What is claimed is:

1. A compound of Formula (I):

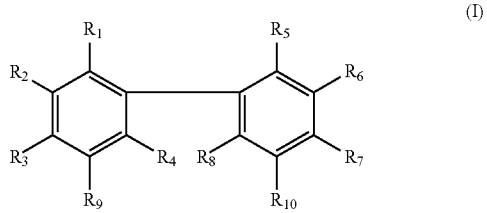

or a salt thereof;
wherein:
$R_1$ and $R_5$ are independently selected from H, OH and alkoxy;
$R_2$-$R_4$ and $R_6$-$R_8$ are independently selected from H, OH, F, Cl, Br, and I;
$R_9$ and $R_{10}$ is $C_2$-$C_8$ alkenyl;
with the proviso that:
at least one of $R_1$, $R_5$ and $R_7$ is OH or alkoxy;
at least one of $R_2$-$R_4$, $R_6$ and $R_8$ is F, Cl, Br or I; and
$R_2$ and $R_6$ are Cl.

2. The compound of claim 1, wherein:
$R_1$ and $R_5$ are independently selected from OH or alkoxy; and
$R_2$ and $R_6$ are independently selected from H, F, Cl, Br and I.

3. The compound of claim 1, wherein $R_1$ and $R_5$ are OH.
4. The compound of claim 1, wherein $R_1$ and $R_7$ are OH.
5. The compound of claim 1, wherein the compound of Formula (I) has the structure of Formula (II):

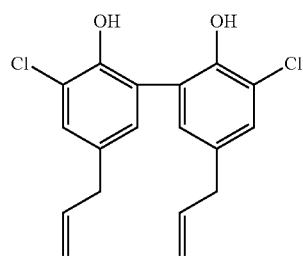

6. The compound of claim 1, wherein the compound of Formula (I) has the structure of Formula (III):

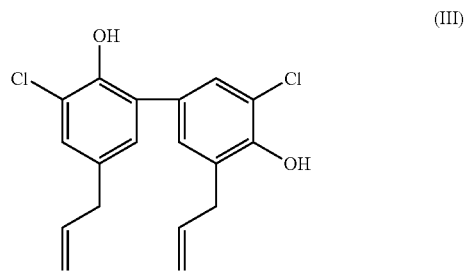 [SMILES: C=CCc1cc(Cl)c(O)c(-c2cc(Cl)c(O)c(CC=C)c2)c1]

7. A composition comprising the compound of claim 1; and a carrier.
8. The composition of claim 7, wherein the carrier is an orally acceptable carrier.
9. The composition of claim 7, wherein the compound of Formula (I) is present at a concentration of from about 0.01 to about 1%, by weight.
10. The composition of claim 7, wherein the compound of Formula (I) is present at a concentration of from about 0.1 to about 0.75%, by weight.
11. The composition of claim 7, wherein the compound of Formula (I) is present at a concentration of about 0.5%, by weight.
12. The composition of claim 7, further comprising one or more components selected from a fluoride ion source; a tartar control agent; a buffering agent; an abrasive; and a combination of two or more thereof.
13. The composition of claim 12, wherein at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.
14. A method of treating or preventing a disease or condition of the oral cavity comprising contacting an oral cavity surface of a subject in need thereof with a composition of claim 7.
15. The method of claim 14, wherein the disease or condition of the oral cavity is selected from gingivitis, periodontitis and halitosis.
16. The composition of claim 7, wherein the carrier is a personal care carrier.
17. A method of treating or preventing a disease or condition of the skin comprising contacting the skin surface of a subject in need thereof with the composition of claim 7.

18. The method of claim 17, wherein the disease or condition is selected from body odor, erythrasma, acne, impetigo, boils, folliculitis, cellulitis, carbuncles, and scalded skin syndrome.

* * * * *